United States Patent
Mignogna et al.

(10) Patent No.: US 10,113,013 B2
(45) Date of Patent: Oct. 30, 2018

(54) CATALYST COMPONENTS FOR THE POLYMERIZATION OF OLEFINS

(71) Applicant: BASELL POLIOLEFINE ITALIA S.R.L., Milan (IT)

(72) Inventors: Alessandro Mignogna, Ferrara (IT); Giampiero Morini, Ferrara (IT)

(73) Assignee: Basell Poliolefine Italia S.r.l., Milan (IT)

( * ) Notice: Subject to any disclaimer, the term of this patent is extended or adjusted under 35 U.S.C. 154(b) by 181 days.

(21) Appl. No.: 15/128,830

(22) PCT Filed: Mar. 24, 2015

(86) PCT No.: PCT/EP2015/056198
§ 371 (c)(1),
(2) Date: Sep. 23, 2016

(87) PCT Pub. No.: WO2015/144668
PCT Pub. Date: Oct. 1, 2015

(65) Prior Publication Data
US 2018/0194870 A1   Jul. 12, 2018

(30) Foreign Application Priority Data
Mar. 26, 2014   (EP) ..................................... 14161750

(51) Int. Cl.
*C08F 4/642* (2006.01)
*C08F 4/02* (2006.01)
*C08F 4/659* (2006.01)
*C08F 110/06* (2006.01)
*C08L 57/00* (2006.01)
*C07C 271/44* (2006.01)
*C08F 10/14* (2006.01)

(52) U.S. Cl.
CPC .......... *C08F 4/6425* (2013.01); *C07C 271/44* (2013.01); *C08F 4/022* (2013.01); *C08F 4/65912* (2013.01); *C08F 110/06* (2013.01); *C08L 57/00* (2013.01); *C08F 10/14* (2013.01); *C08F 2500/15* (2013.01); *C08L 2207/10* (2013.01); *C08L 2314/02* (2013.01)

(58) Field of Classification Search
None
See application file for complete search history.

(56) References Cited

U.S. PATENT DOCUMENTS 9,481,745 B2 * 11/2016 Mignogna ............. C07C 271/12

FOREIGN PATENT DOCUMENTS

| EP | 1866347 A2 | 12/2007 |
|---|---|---|
| EP | 2712875 A1 | 4/2014 |
| WO | WO-2006110234 A2 | 10/2006 |
| WO | WO-2014013401 A1 | 1/2014 |

OTHER PUBLICATIONS

International Search Report and Written Opinion dated Jun. 25, 2015 (Jun. 25, 2015) for Corresponding PCT/EP2015/056198.

* cited by examiner

*Primary Examiner* — Catherine S Branch

(57) ABSTRACT

The present disclosure relates to a solid catalyst component for the polymerization of olefins comprising Mg, Ti and an electron donor of the formula (I):

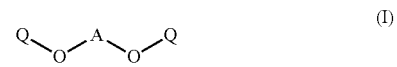

where each Q is a group —COOR$^1$, in which R$^1$ is selected from C$_1$-C$_{15}$ hydrocarbon groups, optionally containing a heteroatom selected from the group consisting of halogens, P, S, N and O; or a group —CON(R$^2$)$_2$, in which R$^2$ groups, equal to or different from each other, are hydrogen or R$^1$ groups which can be fused together to form one or more cycles, and A is a bivalent bridging group with the proviso that the Q groups cannot be simultaneously a group —COOR$^1$ or —CON(R$^2$)$_2$.

15 Claims, No Drawings

CATALYST COMPONENTS FOR THE POLYMERIZATION OF OLEFINS

This application is the U.S. National Phase of PCT International Application PCT/EP2015/056198, filed Mar. 24, 2015, claiming benefit of priority to European Patent Application No. 14161750.6, filed Mar. 26, 2014, the contents of which are incorporated herein by reference in its entirety.

FIELD OF THE INVENTION

The present disclosure relates to catalyst components for the polymerization of olefins, such as propylene, comprising a magnesium (Mg) dihalide based support comprising Ti atoms and an electron donor compound containing a carbonic ester and a carbamate group. The present disclosure further relates to catalysts obtained from the catalyst components and to their use in processes for the polymerization of olefins such as propylene.

BACKGROUND OF THE INVENTION

Catalyst components for the stereospecific polymerization of olefins are known in the chemicals arts. One catalyst family used for the polymerization of olefins such as propylene belongs to the Ziegler-Natta category which generally comprise a solid catalyst component, magnesium dihalide, a titanium compound and an internal electron donor compound, often used in combination with an Al-alkyl compound. When higher crystallinity of the polymer is required, an external donor (for example, an alkoxysilane) may be needed in order to obtain higher isotacticity. One class of internal donors is the esters of phthalic acid, such as diisobutylphthalate. The phthalates are often used as internal donors in combination with alkylalkoxysilanes as external donor. This catalyst system generally gives good performance in terms of activity, isotacticity and xylene insolubility.

However, the use of this catalyst system with phthalates has recently raised concerns due to potential medical issues associated with their use.

Consequently, alternative classes of internal donors for use in the preparation of catalyst components for propylene polymerization have been investigated.

Some alternative catalysts contain donor structures having simultaneously amide groups and ester groups. For instance, WO2006/110234 describes amino acid derivatives including one carbamate group and one free ester function. However, the catalysts generated by these structures have very low activity and stereospecificity in bulk propylene polymerization (please see Table 2).

Another class of internal donors is described in WO2011/068770, which relates to two atom-bridged dicarbonate compounds. According to this document, good results can be obtained when the diol portion is part of a substituted phenyl group, which show interesting stereospecificity but insufficient activity. Moreover, the document discloses that donors having only one carbonate function such as diethyl carbonate have very low performance.

SUMMARY OF THE INVENTION

The present disclosure generally relates to a class of donors containing only one carbonic ester function within a specific structure that generates catalysts showing an excellent balance of activity and stereospecificity when a carbamic/carbamate group is present.

In some embodiments, the present disclosure relates to a catalyst component for the polymerization of olefins comprising Mg, Ti and an electron donor of formula (I):

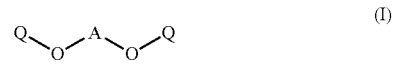

where each Q is a group —COOR$^1$, in which R$^1$ is selected from C$_1$-C$_{15}$ hydrocarbon groups, optionally containing a heteroatom selected from halogen, P, S, N, and O; or a group —CON(R$^2$)$_2$, in which R$^2$ groups, equal to or different from each other, are hydrogen or R$^1$ groups which can be fused together to form one or more cycles, and A is a bivalent bridging group with the proviso that the Q groups cannot simultaneously be a-COOR$^1$ or —CON(R$^2$)$_2$ group.

DETAILED DESCRIPTION OF THE INVENTION

In some embodiments, the catalytic component comprises a group "A" that is a bivalent bridging group with a chain length between the two bridging bonds of 1-10 atoms. In case of cyclic structures acting as bridging groups, the term "chain length" refers to the shortest sequence of atoms bridging the oxygen atoms of formula (I). In a general embodiment, the bridging group has the formula —(ZR$^3$m) n-, in which, independently, Z is selected from C, Si, Ge, O, N, S or P, and the R$^3$ groups, equal to or different from each other, are hydrogen or a C$_1$-C$_{20}$ hydrocarbon radical, optionally containing a heteroatom selected from halogen, P, S, N, O and Si, which can be fused together to form one or more cycles, and m is a number satisfying the valences of Z and n is an integer ranging from 1 to 10. In certain embodiments, in the bridging group of formula —(ZR3m)n- the atoms O, S, and N are not directly linked to the oxygen of formula (I), i.e. they are not the terminal atoms of the bridging group. In some embodiments, Z is selected from carbon (C) and silicon (Si).

In one embodiment, the bivalent bridging group is selected from the group consisting of aliphatic, alicyclic and aromatic bivalent radicals, optionally substituted with C$_1$-C$_{15}$ hydrocarbon groups and/or with heteroatoms selected from halogen, P, S, N, O and Si, and having a bridging chain length ranging from 1 to 6 atoms, such as from 1 to 4 atoms.

In a further embodiment, the bridging group is an aliphatic or alicyclic bridging group having a bridging chain length of 1-6 carbon atoms. Among this class, bridging groups of the formula —(CR$^4_p$)$_s$—, in which R$^4$ is independently hydrogen or a C$_1$-C$_{20}$ hydrocarbon radicals, optionally substituted with heteroatoms selected from halogen, P, S, N, O and Si, and which can be fused together to form one or more cycles, where p is a number satisfying the available valence of carbon and s is a number from 1 to 6, such as from 1 to 4, may be used. Examples of bridging groups are methylidene (methylene), ethane-1,2-diyl, butane-2,3-diyl, pentane-2,4-diyl, 2,2-diisobutylpropane-1,3-diyl, cyclohexane-1,2-diyl and cyclopentane-1,2-diyl.

Another class of bridging groups for use in the present technology is the one based on aromatic groups which, viae carbon ring atoms, can link the two oxygen atoms of formula (I). Among them, the phenyl groups, optionally substituted with halogens or C$_1$-C$_{20}$ alkyl radicals, bridging the oxygen atoms in position 1,2 or 1,3 or 1,4, and the naphthalene groups, optionally substituted bridging the oxygen groups in position 1,2 or 2,3 or 1,8, may be used.

In some embodiments, internal electron donors are those of the formula (II) below:

$$\text{(II)}$$

[Structure of formula (II): benzene ring with Q-O- groups at positions 1,2 and $R^5$ groups at positions 3,4,5,6]

in which the Q groups may comprise —COOR$^1$, in which R$^1$ is selected from C$_1$-C$_{15}$ hydrocarbon groups, optionally containing a heteroatom selected from halogen, P, S, N, and O; or a group —CON(R$^2$)$_2$, in which R$^2$ groups, equal to or different from each other, are hydrogen or R$^1$ groups which can be fused together to form one or more cycles, and R$^5$, independently, is selected from hydrogen, halogens or C$_1$-C$_{15}$ hydrocarbon groups optionally substituted with heteroatoms selected from halogen, P, S, N, O and Si, with the proviso that at least one of R$^5$ is different from hydrogen.

In certain embodiments, structures of the formula (II) are those in which at least two of the R$^5$ groups are different from hydrogen. In further embodiments, the aromatic ring of formula (II) is substituted in position 3,5 and/or 6. In all these cases, R$^5$ groups may be selected from C$_1$-C$_5$ alkyl groups, including substitution in position 3 and/or 6 with a primary alkyl group such as methyl, and in position 4 and/or 5 with a tertiary alkyl group including tert-butyl.

Specific examples of aromatic bridging groups for use in the present technology include 1,2-phenylene, 3-methyl-1,2-phenylene, 4-chloro-1,2-phenylene, 4-(tert-butyl)-1,2-phenylene, 3,6-dimethyl-1,2-phenylene, 3,5-dimethyl-1,2-phenylene, 5-(tert-butyl)-3-methyl-1,2-phenylene, and 3,5-diisopropyl-1,2-phenylene.

In some embodiments, the formulas (I) and (II) comprise R$^1$ and R$^2$ groups independently selected from C$_1$-C$_{15}$ alkyl groups, C$_6$-C$_{14}$ aryl groups, C$_3$-C$_{15}$ cycloalkyl groups, and C$_7$-C$_{15}$ arylalkyl or alkylaryl groups; while R$^2$ groups can additionally comprise hydrogen. In further embodiments, the R$^1$ groups in formulas (I) and (II) are alkyl groups such as C$_1$-C$_5$ alkyl groups.

In additional embodiments, the formulas (I) and (II) comprise R$^2$ groups that are independently selected from hydrogen or C$_1$-C$_{10}$ alkyl groups, including hydrogen or C$_1$-C$_5$ alkyl groups such as ethyl groups.

In some embodiments, subgroups are those represented by the formula (III) below:

$$\text{(III)}$$

[Structure of formula (III): benzene ring with Q-O- groups at positions 1,2 and an $R^5$ group]

in which R$^5$ is a branched alkyl group such as t-butyl.

Because each of the Q groups can be selected from —COOR$^1$ and CON(R$^2$)$_2$, but cannot simultaneously comprise a group —COOR$^1$ or —CON(R$^2$)$_2$, the compounds of formula (III) can exist in two different isomeric forms.

In some embodiments, formula (III) comprises R$^1$ and R$^2$ groups that are C$_1$-C$_5$ alkyl groups, including linear C$_1$-C$_5$ alkyl groups such as ethyl and n-propyl groups.

In additional embodiments, the final amount of electron donor compound in the solid catalyst component ranges from 1 to 25% by weight, such as from 3 to 20% by weight.

Non-limiting examples of structures of formulas (I), (II) and (III) include (9-(((ethoxycarbonyl)oxy)methyl)-9H-fluoren-9-yl)methyl diethylcarbamate, 2-((ethoxycarbonyl)oxy)-3,6-dimethylphenyl diethylcarbamate, 2-((ethoxycarbonyl)oxy)-3,6-dimethylphenyl dimethylcarbamate, 2-((ethoxycarbonyl)oxy)-3,6-dimethylphenyl ethylcarbamate, 2-((ethoxycarbonyl)oxy)-3-methylphenyl diethylcarbamate, 2-((ethoxycarbonyl)oxy)-3-methylphenyl dimethylcarbamate, 2-((ethoxycarbonyl)oxy)-3-methylphenyl ethylcarbamate, 2-((ethoxycarbonyl)oxy)-4-methylphenyl diethylcarbamate, 2-((ethoxycarbonyl)oxy)-4-methylphenyl dimethylcarbamate, 2-((ethoxycarbonyl)oxy)-4-methylphenyl ethylcarbamate, 2-((ethoxycarbonyl)oxy)-5-methylphenyl diethylcarbamate, 2-((ethoxycarbonyl)oxy)-5-methylphenyl dimethylcarbamate, 2-((ethoxycarbonyl)oxy)-5-methylphenyl ethylcarbamate, 2-((ethoxycarbonyl)oxy)-6-methylphenyl dimethylcarbamate, 2-((ethoxycarbonyl)oxy)-6-methylphenyl ethylcarbamate, 2-((ethoxycarbonyl)oxy)phenyl diethylcarbamate, 2-((ethoxycarbonyl)oxy)phenyl dimethylcarbamate, 2-((ethoxycarbonyl)oxy)phenyl ethylcarbamate, 3-(tert-butyl)-6-((ethoxycarbonyl)oxy)-2,5-dimethylphenyl diethylcarbamate, 3-(tert-butyl)-6-((ethoxycarbonyl)oxy)-2,5-dimethylphenyl dimethylcarbamate, 3-(tert-butyl)-6-((ethoxycarbonyl)oxy)-2,5-dimethylphenyl ethylcarbamate, 4-((ethoxycarbonyl)oxy)pentan-2-yl diethylcarbamate, 4-(tert-butyl)-2-((ethoxycarbonyl)oxy)-3,6-dimethylphenyl diethylcarbamate, 4-(tert-butyl)-2-((ethoxycarbonyl)oxy)-3,6-dimethylphenyl dimethylcarbamate, 4-(tert-butyl)-2-((ethoxycarbonyl)oxy)-3,6-dimethylphenyl ethylcarbamate, 4-(tert-butyl)-2-((ethoxycarbonyl)oxy)-6-methylphenyl diethylcarbamate, 4-(tert-butyl)-2-((ethoxycarbonyl)oxy)-6-methylphenyl dimethylcarbamate, 4-(tert-butyl)-2-((ethoxycarbonyl)oxy)-6-methylphenyl dipropylcarbamate, 4-(tert-butyl)-2-((ethoxycarbonyl)oxy)-6-methylphenyl ethylcarbamate, 4-(tert-butyl)-2-((ethoxycarbonyl)oxy)phenyl diethylcarbamate, 4-(tert-butyl)-2-((ethoxycarbonyl)oxy)phenyl dimethylcarbamate, 4-(tert-butyl)-2-((ethoxycarbonyl)oxy)phenyl dipropylcarbamate, 4-(tert-butyl)-2-((ethoxycarbonyl)oxy)phenyl ethylcarbamate, 5-(tert-butyl)-2-((ethoxycarbonyl)oxy)-3-methylphenyl diethylcarbamate, 5-(tert-butyl)-2-((ethoxycarbonyl)oxy)-3-methylphenyl dimethylcarbamate, 5-(tert-butyl)-2-((ethoxycarbonyl)oxy)-3-methylphenyl dipropylcarbamate, 5-(tert-butyl)-2-((ethoxycarbonyl)oxy)-3-methylphenyl ethylcarbamate, 5-(tert-butyl)-2-((ethoxycarbonyl)oxy)phenyl diethylcarbamate, 5-(tert-butyl)-2-((ethoxycarbonyl)oxy)phenyl dimethylcarbamate, 5-(tert-butyl)-2-((ethoxycarbonyl)oxy)phenyl dipropylcarbamate, 5-(tert-butyl)-2-((ethoxycarbonyl)oxy)phenyl ethylcarbamate, 6-((ethoxycarbonyl)oxy)cyclohexa-1,2,3,5-tetraen-1-yl diethylcarbamate, 8-((ethoxycarbonyl)oxy)naphthalen-1-yl diethylcarbamate 2-((butoxycarbonyl)oxy)-4-(tert-butyl)-6-methylphenyl diethylcarbamate, 2-((butoxycarbonyl)oxy)-5-(tert-butyl)-3-methylphenyl diethylcarbamate, 4-(tert-butyl)-2-((isobutoxycarbonyl)oxy)-6-methylphenyl diethylcarbamate, 5-(tert-butyl)-2-((isobutoxycarbonyl)oxy)-3-methylphenyl diethylcarbamate, 2-((ethoxycarbonyl)oxy)-3-methylphenyl dipropylcarbamate, and 2-((ethoxycarbonyl)oxy)-6-methylphenyl dipropylcarbamate.

The internal donors disclosed above can be generally prepared by reacting an excess of a starting diol HO-A-OH with a suitable carbamoyl chloride, followed by removal of the unreacted diol by aqueous washings, distillation or chromatographic techniques. The resulting monocarbamate-monoalcohol is reacted with a suitable chloroformate or carbonate. Both steps are carried out in presence of a base, and the order of reaction can be inverted. Alternately, the internal donor can be prepared by converting the diol into a cyclic carbonate. This cyclic carbonate may then be reacted with a primary or secondary amine, and the product reacted with a chloroformate or carbonate.

In certain embodiments, the amount of Ti atoms in the solid catalyst component is higher than 1.5% by weight, including higher than 2.0% by weight, with respect to the total weight of the catalyst component.

As described above, the catalyst components of the present disclosure may comprise, in addition to the above referenced electron donors, Ti, Mg and a halogen. In some embodiments, the catalyst components comprise a titanium compound, having at least a Ti-halogen bond, with the above referenced electron donor compounds supported on a Mg-halide composition. In certain embodiments, the magnesium halide is $MgCl_2$ in active form, which is known from the patent literature as a support for Ziegler-Natta catalysts. U.S. Pat. Nos. 4,298,718 and 4,495,338 were the first to describe the use of these compounds in Ziegler-Natta catalysis. It is known from these patents that magnesium dihalides in active form and used as supports or co-supports in components of catalysts for the polymerization of olefins are characterized by X-ray spectra in which the most intense diffraction line of the non-active halide is diminished in intensity and is replaced by a halo whose maximum intensity is displaced towards lower angles, relative to that of the more intense line.

Titanium compounds that may be used in the catalyst component of the present disclosure include $TiCl_4$ and $TiCl_3$. Ti-haloalcoholates of the formula $Ti(OR)_{m-y}X_y$ can also be used, where m is the valence of titanium, y is a number between 1 and m−1, X is a halogen and R is a hydrocarbon radical having from 1 to 10 carbon atoms.

The preparation of the solid catalyst component can be carried out according to several methods, including the reaction between magnesium alcoholates or chloroalcoholates as described in U.S. Pat. No. 4,220,554, and an excess of $TiCl_4$ in the presence of the electron donor compounds at a temperature from about 80 to about 130° C.

According to one method, the solid catalyst component can be prepared by reacting a titanium compound of formula $Ti(OR)_{m-y}X_y$, where m is the valence of titanium and y is a number between 1 and m, such as $TiCl_4$, with a magnesium chloride derived from an adduct of the formula $MgCl_2 \cdot pROH$, where p is a number between 0.1 and 6, such as from 2 to 3.5, and R is a hydrocarbon radical having 1-18 carbon atoms. The adduct can be prepared in spherical form by mixing alcohol and magnesium chloride in the presence of an inert hydrocarbon immiscible with the adduct that is operated under stirring conditions at the melting temperature of the adduct (e.g. 100-130° C.). The emulsion is quickly quenched, thereby causing the solidification of the adduct in the form of spherical particles. Examples of spherical adducts prepared according to this procedure are described in U.S. Pat. Nos. 4,399,054 and 4,469,648. The resulting adducts can be directly reacted with a Ti compound or subjected to thermally controlled dealcoholation at a temperature from about 80-130° C. to obtain an adduct in which the number of moles of alcohol is generally lower than 3, such as between 0.1 and 2.5. The reaction with the Ti compound can be carried out by suspending the adduct (optionally dealcoholated) in cold $TiCl_4$ (generally at a temperature of about 0° C.); the mixture is heated up to 80-130° C. and kept at this temperature for 0.5-2 hours. The treatment with $TiCl_4$ can be carried out one or more times. The electron donor compound may be added during the treatment with $TiCl_4$. The preparation of catalyst components in spherical form are described, for example, in European Patent Applications EP-A-395083, EP-A-553805, EP-A-553806, EPA601525 and WIPO Pat. App. Pub. No. WO98/44001.

The solid catalyst components obtained according to the above method are characterized by a surface area (by B.E.T. method) generally between 20 and 500 $m^2/g$, including between 50 and 400 $m^2/g$, and a total porosity (by B.E.T. method) higher than 0.2 $cm^3/g$, such as between 0.2 and 0.6 $cm^3/g$. The porosity (Hg method) due to pores with radius up to 10.000 Å generally ranges from 0.3 to 1.5 $cm^3/g$, including from 0.45 to 1 $cm^3/g$.

The solid catalyst component has an average particle size ranging from 5 to 120 µm, such as from 10 to 100 µm.

In any of these preparation methods the electron donor compounds can be added as commercially available or they can be obtained in situ by using an appropriate precursor capable of producing the desired electron donor compound by known chemical reactions.

In some embodiments, the final amount of the electron donor compound of formula (I) is such that its molar ratio with respect to the Ti atoms is from 0.01 to 2, such as from 0.05 to 1.5.

The solid catalyst components according to the present disclosure are converted into catalysts for the polymerization of olefins by reacting the components with organoaluminum compounds according to known methods.

In some embodiments, the present disclosure relates to a catalyst for the polymerization of olefins of the formula $CH_2=CHR$, in which R is hydrogen or a hydrocarbyl radical with 1-12 carbon atoms, comprising the product obtained by contacting:
(i) the solid catalyst component as disclosed above,
(ii) an alkylaluminum compound and, optionally,
(iii) an external electron donor compound.

The alkyl-Al compound (ii) may be chosen from among the trialkyl aluminum compounds such as, for example, triethylaluminum, triisobutylaluminum, tri-n-butylaluminum, tri-n-hexylaluminum and tri-n-octylaluminum. It is also possible to use alkylaluminum halides, alkylaluminum hydrides or alkylaluminum sesquichlorides, such as $ALEt_2CL$ and $Al_2Et_3Cl_3$, optionally in mixtures with the above referenced trialkylaluminum compounds.

Suitable external electron-donor compounds include silicon compounds, ethers, esters, amines, heterocyclic compounds, 2,2,6,6-tetramethylpiperidine and ketones.

Another class of external donor compounds for use in the present technology is that of silicon compounds of the formula $(R_7)_a(R_8)_bSi(OR_9)_c$, where a and b are integers from 0 to 2, c is an integer from 1 to 4 and the sum (a+b+c) is 4; and $R_7$, $R_8$, and $R_9$, are radicals with 1-18 carbon atoms that optionally contain heteroatoms. In certain embodiments, silicon compounds in which a is 1, b is 1, c is 2, at least one of $R_7$ and $R_8$ is selected from branched alkyl, cycloalkyl or aryl groups with 3-10 carbon atoms optionally containing heteroatoms and $R_9$ is a $C_1$-$C_{10}$ alkyl group, such as methyl, may be used. Examples of such silicon compounds are methylcyclohexyldimethoxysilane (C donor), diphenyldimethoxysilane, methyl-t-butyldimethoxysilane, dicyclopentyldimethoxysilane (D donor), diisopropyldimethoxysilane, (2-ethylpiperidinyl)t-butyldimethoxysilane, (2-ethylpiperidinyl)thexyldimethoxysilane, (3,3,3-trifluoro-n-propyl)(2-ethylpiperidinyl)dimethoxysilane, methyl(3,3,3-trifluoro-n-propyl)dimethoxysilane, and N,N-diethylaminotriethoxysilane. In additional embodiments, silicon compounds in which a is 0, c is 3, $R_8$ is a branched alkyl or cycloalkyl group, optionally containing heteroatoms, and $R_9$ is methyl may be used. Examples of such silicon compounds are cyclohexyltrimethoxysilane, t-butyltrimethoxysilane and thexyltrimethoxysilane.

In some embodiments, the electron donor compound (iii) is used in such an amount to give a molar ratio between the organoaluminum compound and the electron donor compound (iii) of from 0.1 to 500, such as from 1 to 300 and from 3 to 100.

A further object of the present disclosure includes a process for the (co)polymerization of olefins $CH_2=CHR$, in which R is hydrogen or a hydrocarbyl radical with 1-12 carbon atoms, carried out in the presence of a catalyst comprising the product of the reaction between:
(i) the solid catalyst component of the disclosure,
(ii) an alkylaluminum compound, and
(iii) optionally, an electron-donor compound (external donor).

The polymerization process can be carried out according to known techniques, for example, slurry polymerization using an inert hydrocarbon solvent as a diluent, or bulk polymerization using the liquid monomer (for example, propylene) as the reaction medium. Moreover, it is possible to carry out the polymerization process in gas-phase in one or more fluidized or mechanically agitated bed reactors.

The polymerization is generally carried out at temperature of from 20 to 120° C., such as from 40 to 80° C. When the polymerization is carried out in gas-phase, the operating pressure is generally between 0.5 and 5 MPa, including between 1 and 4 MPa. In the bulk polymerization, the operating pressure is generally between 1 and 8 MPa, such as between 1.5 and 5 MPa.

In the polymerization of propylene using the catalyst of the present disclosure and under the standard polymerization conditions described in the experimental section, it is possible to obtain polymerization activities ranging from 50 to 90 kg/g cat. In some embodiments, the resulting polymers are characterized by high polymer isotacticity expressed by a value of xylene insoluble matter of higher than 98.5% preferably higher than 99% wt.

The following examples are given in order to further illustrate embodiments of the present disclosure without limiting it.

Characterizations

Determination of X.I.

2.5 g of polymer and 250 ml of o-xylene were placed in a round-bottomed flask provided with a cooler and a reflux condenser and kept under nitrogen. The mixture was heated to 135° C. and kept under stirring conditions for about 60 minutes. The final solution was allowed to cool to 25° C. under continuous stirring, and the insoluble polymer was filtered. The filtrate was evaporated in a nitrogen flow at 140° C. to reach a constant weight. The content of the xylene-soluble fraction is expressed as a percentage of the original 2.5 grams and then, by calculating the difference, the X.I. %.

Determination of Donors

The content of electron donor(s) was determined via gas chromatography (GC). The solid component was dissolved in acidic water. The resulting solution was extracted with ethyl acetate, an internal standard was added, and a sample of the organic phase was analyzed via gas chromatography to determine the amount of donor present at the starting catalyst compound.

Melt Flow Rate (MFR/MIL)

The melt flow rate (MFR/MIL) of the polymer was determined according to ISO 1133 (230° C., 2.16 kg).

EXAMPLES

Synthetic Example 1

Mixture of 4-(tert-butyl)-2-((ethoxycarbonyl)oxy)-6-methylphenyl diethylcarbamate and 5-(tert-butyl)-2-((ethoxycarbonyl)oxy)-3-methylphenyl diethylcarbamate First Step:

In a 500 cm³ round bottom flask, under nitrogen, THF (240 cm³), 3-methyl-5-tert-butyl-catechol (30 g, 0.166 mol), triethylamine (51 cm3, 0.366 mol) were added, and dichloroacetyl chloride (33.7 cm³, 0.350 mol) is added dropwise with cooling. After 1 hour at room temperature the mixture is quenched with aqueous HCl, extracted with ethyl acetate and washed with water until a neutral pH is reached. The solution is anhydrified over $Na_2SO_4$ and the solvent is distilled off, resulting in 67 g of the white solid 5-(tert-butyl)-3-methyl-1,2-phenylene bis(2,2-dichloroacetate (percent yield: 99%).

Second Step:

In a 1 dm³ round bottom flask, under nitrogen, THF (330 cm³), NaH (7.85 g, 0.327 mol) are mixed, and a solution of 5-(tert-butyl)-3-methyl-1,2-phenylene bis(2,2-dichloroacetate (62.6 g, 0.156 mol) dissolved in THF (50 cm³) is added dropwise at room temperature. The dark brown mixture is stirred at room temperature until GC shows that the reaction is completed (time=43 hours). Then the mixture is quenched with water, diethyl ether is added and the organic layer is washed with aqueous $NaHCO_3$. The resulting solution is anhydrified over $Na_2SO_4$ and the solvent is distilled off to afford a dark brown crude which is distilled at reduced pressure To produce 25.1 g of a yellow solid comprising pure 6-(tert-butyl)-4-methylbenzo[d][1,3]dioxol-2-one (percent yield: 77%).

Third Step:

In a 500 cm³ round bottom flask, under nitrogen, are introduced THF (175 cm³) and 6-(tert-butyl)-4-methylbenzo[d][1,3]dioxol-2-one (25 g, 0.117 mol). The mixture is cooled down to −5° C., and diethylamine is added dropwise (6.9 cm³, 0.330 mol). The mixture is brought to room temperature and, after one hour of stirring, triethylamine (14.7 cm³, 0.145 mol) and ethyl chloroformate (18 cm³, 0.145 mol) are added sequentially with cooling. After one hour the reaction is quenched with aqueous HCl, extracted with ethyl acetate and washed with water until a neutral pH is achieved. The resulting solution is anhydrified over $Na_2SO_4$ and the solvent is distilled off, resulting in 41.2 g of a mixture of 4-(tert-butyl)-2-((ethoxycarbonyl)oxy)-6-methylphenyl diethylcarbamate and 5-(tert-butyl)-2-((ethoxycarbonyl)oxy)-3-methylphenyl diethylcarbamate (percent yield: 96%).

Synthetic Example 2

Mixture of 4-(tert-butyl)-2-((ethoxycarbonyl)oxy)-6-methylphenyl dipropylcarbamate and 5-(tert-butyl)-2-((ethoxycarbonyl)oxy)-3-methylphenyl dipropylcarbamate The procedure is the same as that of Synthetic Example 1 except that dipropylamine is used instead of diethylamine in the third step.

Synthetic Example 3

Mixture of 2-((ethoxycarbonyl)oxy)-3-methylphenyl diethylcarbamate and 2-((ethoxycarbonyl)oxy)-6-methylphenyl diethylcarbamate The procedure is the same of Synthetic Example 1 except that 3-methylcatechol is used instead of 3-methyl-5-tert-butyl-catechol in the first step.

Comparative Synthetic Example 4

5-(tert-butyl)-3-methyl-1,2-phenylene diethyl dicarbonate

The synthesis of 5-(tert-butyl)-3-methyl-1,2-phenylene diethyl dicarbonate has been done according to the general preparation described in U.S. Pat. App. Pub. No. 2011/0130530.

Synthetic Example 5

Mixture of 2-((butoxycarbonyl)oxy)-4-(tert-butyl)-6-methylphenyl diethylcarbamate and 2-((butoxycarbonyl)oxy)-5-(tert-butyl)-3-methylphenyl diethylcarbamate The procedure is the same as that of Synthetic Example 1 except that butyl chloroformate is used instead of ethyl chloroformate in the third step.

Synthetic Example 6

Mixture of 4-(tert-butyl)-2-((isobutoxycarbonyl)oxy)-6-methylphenyl diethylcarbamate and 5-(tert-butyl)-2-((isobutoxycarbonyl)oxy)-3-methylphenyl diethylcarbamate The procedure is the same as that of Synthetic Example 1 except that isobutyl chloroformate is used instead of ethyl chloroformate in the third step.

Synthetic Example 7

Mixture of 2-((ethoxycarbonyl)oxy)-3-methylphenyl dipropylcarbamate and 2-((ethoxycarbonyl)oxy)-6-methylphenyl dipropylcarbamate The procedure is the same of Synthetic Example 1 except that 3-methylcatechol is used instead of 3-methyl-5-tert-butyl-catechol in the first step, and dipropylamine is used instead of diethylamine in the third step.

Synthetic Example 8

Mixture of 4-(tert-butyl)-2-((ethoxycarbonyl)oxy)phenyl diethylcarbamate and 5-(tert-butyl)-2-((ethoxycarbonyl)oxy)phenyl diethylcarbamate The procedure is the same of Synthetic Example 1 except that 4-tert-butyl-catechol is used instead of 3-methyl-5-tert-butyl-catechol in the first step.

General Procedure for Preparation of the Spherical Adducts A and B

An initial amount of microspheroidal $MgCl_2 \cdot 2.8C_2H_5OH$ was prepared according to the method described in Example 2 of WIPO Pat. App. Pub. No. WO98/44009, but on a larger scale. This adduct is called "adduct A". The solid adduct A was then subject to thermal dealcoholation at increasing temperatures from 30 to 130° C. in a nitrogen current until reaching an alcohol content of 1.9 moles per mol of $MgCl_2$. This partially dealcoholated adduct is called "adduct B."

General Procedure for the Polymerization of Propylene

A 4-liter steel autoclave equipped with a stirrer, pressure gauge, thermometer, catalyst feeding system, monomer feeding lines and thermostating jacket, was purged with nitrogen flow at 70° C. for one hour. Then, at 30° C. under propylene flow, were charged (in sequence) 75 mL of anhydrous hexane, 0.76 g of $AlEt_3$, the external electron donor indicated in Table 1 (if used) and 0.006-0.010 g of solid catalyst component. The autoclave was closed and 2.0 NL of hydrogen were added. Then, under stirring, 1.2 kg of liquid propylene was fed. The temperature was raised to 70° C. over five minutes and the polymerization was carried out at this temperature for two hours. At the end of the polymerization, the non-reacted propylene was removed; the polymer was recovered and dried at 70° C. under vacuum for three hours. Then the polymer was weighed and fractionated with o-xylene to determine the amount of the xylene insoluble (X.I.) fraction.

Example 1

Preparation of the Solid Catalyst Component and Polymerization

Into a 500 $cm^3$ round bottom flask, equipped with mechanical stirrer, cooler and thermometer, 250 $cm^3$ of $TiCl_4$ were introduced at room temperature under a nitrogen atmosphere. After cooling to 0° C., while stirring, the internal donor of Synthetic Example 1 and 10.0 g of the spherical adduct A were sequentially added into the flask. The amount of charged internal donor was such that a Mg/donor molar ratio of 6 was produced. The temperature was raised to 100° C. and maintained for 2 hours. Thereafter, stirring was stopped, the solid product was allowed to settle and the supernatant liquid was siphoned off at 100° C. After the supernatant was removed, fresh $TiCl_4$ was added to reach the initial liquid volume. The mixture was then heated at 120° C. and kept at this temperature for 1 hour. Stirring was stopped, the solid was allowed to settle and the supernatant liquid was siphoned off. The solid was washed with anhydrous hexane six times (6×100 $cm^3$) with a temperature gradient decreasing to 60° C., and washed with anhydrous hexane one time (100 $cm^3$) at room temperature. The resulting solid was then dried under vacuum and analyzed. The solid catalyst component contains 4.3% wt of Ti and 18.0% wt of internal donor. The solid catalyst components were evaluated for their ability in the polymerization of propylene using the procedure described above. The results are listed in Table 1.

Example 2

Preparation of the Solid Catalyst Component and Polymerization

The procedure described above for the solid catalyst component 1 was repeated, using the donor of Synthetic Example 2 as internal donor. The solid catalyst components were tested for their performance in the polymerization of propylene using the procedure described above. The results are listed in Table 1.

Example 3

Preparation of Solid Catalyst Component and Polymerization

The procedure described above for solid catalyst component 1 was repeated, using the donor prepared in Synthetic Example 3. The solid catalyst components were tested for their performance in the polymerization of propylene using the procedure described above. The results are listed in Table 1.

Example 4

Preparation of Solid Catalyst Component and Polymerization

Into a 500 cm$^3$ round bottom flask, equipped with mechanical stirrer, cooler and thermometer 250 cm$^3$ of TiCl$_4$ were introduced at room temperature under a nitrogen atmosphere. After cooling to 0° C. and while stirring, the internal donor prepared in Synthetic Example 1 and 10.0 g of the spherical adduct B were sequentially added into the flask. The amount of charged internal donor was added to produce a Mg/donor molar ratio of 8. The temperature was raised to 120° C. and maintained for 1 hour. Thereafter, stirring was stopped, the solid product was allowed to settle and the supernatant liquid was siphoned off at 120° C. After the supernatant was removed, additional fresh TiCl$_4$ was added to reach the initial liquid volume again. The mixture was then heated at 120° C. and kept at this temperature for 30 minutes. Stirring was stopped, the solid was allowed to settle and the supernatant liquid was siphoned off. After the supernatant was removed, fresh TiCl$_4$ was added to reach the initial liquid volume. The mixture was then heated at 120° C. and kept at this temperature for 15 minutes. Stirring was stopped, the solid was allowed to settle and the supernatant liquid was siphoned off. The solid was washed four times with anhydrous heptane (4×100 cm$^3$) at 90° C. and two times with anhydrous iso-hexane (2×100 cm$^3$) at 25° C., then dried under vacuum. The resulting solid catalyst component contains 3.2% wt of Ti, and 14.4% wt of internal donor. The solid catalyst components were evaluated for their performance in the polymerization of propylene using the procedure described above. The results are listed in Table 1.

Examples 5-8

The procedure described above for solid catalyst component 1 was repeated, using the donors prepared in Synthetic Examples 5-8, respectively. The solid catalyst components were evaluated for their performance in the polymerization of propylene, using the procedure described above. The results and the catalyst composition are reported in Table 1.

Comparative Example 1

Preparation of Solid Catalyst Component and Polymerization

The procedure described above for solid catalyst component 1 was repeated, using the donor prepared according to Comparative Synthetic Example 4 as the internal donor. The solid catalyst component contains 2.6% wt of Ti and 20.7% wt of internal donor. The solid catalyst components were evaluated for their performance in the polymerization of propylene using the procedure described above. The results are listed in Table 1.

Comparative Example 2

Preparation of Solid Catalyst Component 6 (ID=N-cbz-L-proline methyl ester)

The procedure described above for solid catalyst component 1 was repeated using commercially available (Sigma-Aldrich) N-cbz-L-proline methyl ester. The solid catalyst component contains 5.4% wt of Ti. The solid catalyst components were evaluated for their performance in the polymerization of propylene, using the procedure described above. The results are listed in Table 1.

TABLE 1

| EX | Catalyst composition | | Polymerization | | |
|---|---|---|---|---|---|
| | ID % wt | Ti % wt | ED | Activity kg/g | XI % wt | MIL S/10' |
| 1 | 18 | 4.3 | D | 75 | 99.2 | 0.5 |
| | " | " | C | 82 | 98.9 | 0.3 |
| | " | " | No ED | 97 | 96.3 | 0.4 |
| 2 | 14.5 | 4 | D | 75 | 99.2 | 0.6 |
| 3 | 17.2 | 3.6 | D | 50 | 98.3 | 1.5 |
| 4 | 14.4 | 3.2 | D | 81 | 98.8 | 0.9 |
| | " | " | C | 80 | 98.7 | 0.4 |
| | " | " | No ED | 122 | 94.4 | 1.4 |
| C1 | 20.7 | 2.6 | D | 36 | 98.5 | 3.6 |
| C2 | n.d | 5.4 | D | 13 | 93.1 | 6.9 |
| 5 | n.d. | 4.4 | D | 76 | 98.9 | 0.8 |
| 6 | n.d. | 4.6 | D | 58 | 98.6 | 0.7 |
| 7 | n.d. | 3.9 | D | 51 | 98.1 | 2.8 |
| 8 | 17.9 | 3.2 | D | 59 | 98.9 | 0.4 |

ED: External Donor
D: Dicyclopentyldimethoxysilane
C: Methylcyclohexyldimethoxysilane

What is claimed is:

1. A solid catalyst component for the polymerization of olefins comprising Mg, Ti and an electron donor of the formula (I):

(I)

where each Q is a group —COOR$^1$ in which R$^1$ is selected from C$_1$-C$_{15}$ hydrocarbon groups, optionally containing a heteroatom selected from the group consisting of a halogen, P, S, N, and O; or a group —CON(R$^2$)$_2$ in which R$^2$ groups, equal to or different from each other, are selected from hydrogen or R$^1$ groups which are optionally fused together to form one or more cycles; and A is a bivalent bridging group with the proviso that the Q groups cannot be simultaneously a group —COOR$^1$ or —CON(R$^2$)$_2$.

2. The catalyst component of claim 1, wherein A is a bivalent bridging group with a chain length between the two free radicals of 1-10 atoms.

3. The catalyst component of claim 1, wherein the bridging group has the formula —(ZR$^3_m$)$_n$— in which, independently, Z is selected from the group consisting of C, Si, Ge, O, N, S and P, the R$^3$ groups, equal to or different from each other, are hydrogen or C$_1$-C$_{20}$ hydrocarbon radicals, optionally containing a heteroatom selected from the group consisting of halogen, P, S, N, O and Si, which are optionally fused together to form one or more cycles, m is a number satisfying the valences of Z and n is an integer ranging from 1 to 10.

4. The catalyst component of claim 3, wherein the bridging group contains an aromatic group, wherein at least two carbon atoms of the aromatic are covalently bonded to the two oxygen atoms of formula (I).

5. The catalyst component of claim 4, wherein the bridging group is selected from phenyl groups, optionally substituted with halogens or C$_1$-C$_{20}$ alkyl radicals, bridging the oxygen atoms in position 1,2 or 1,3 or 1,4 and from naphthalene groups, optionally substituted by bridging the oxygen groups in position 1,2 or 2,3 or 1,8.

6. The catalyst component of claim 1, wherein the donor is selected from the compounds of formula (II)

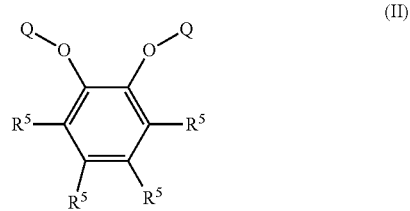

(II)

in which Q is defined as in claim 1, and R$^5$, independently, is selected from the group consisting of hydrogen, the halogens and C$_1$-C$_{15}$ hydrocarbon groups, optionally substituted with heteroatoms selected from the group consisting of the halogens, P, S, N, O and Si, with the proviso that at least one of R$^5$ is different from hydrogen.

7. The catalyst component of claim 6, wherein at least two of the R$^5$ groups are different from hydrogen.

8. The catalyst component of claim 7, wherein the aromatic ring of formula (II) is substituted in position 3,5 with R$^5$ groups selected from C$_1$-C$_5$ alkyl groups.

9. The catalyst component of claim 1, wherein the R$^1$ and R$^2$ groups are independently selected from C$_1$-C$_{15}$ alkyl groups, C$_6$-C$_{14}$ aryl groups, C$_3$-C$_{15}$ cycloalkyl groups, and C$_7$-C$_{15}$ arylalkyl or alkylaryl groups; with the proviso that the R$^2$ groups can also be hydrogen.

10. The catalyst component of claim 6, wherein the donor is selected from the compounds of formula (III):

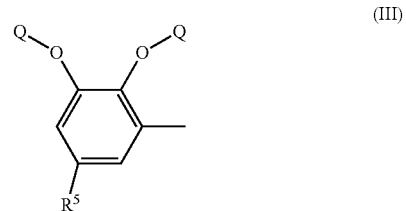

(III)

wherein Q is defined as in claim 1, and R$^5$ is a branched alkyl group.

11. The catalyst component of claim 10, wherein R$^1$ and R$^2$ are C$_1$-C$_5$ alkyl groups, and R$^5$ is a t-butyl group.

12. A catalyst for the polymerization of olefins comprising the product of the reaction between:
(i) the solid catalyst component of claim 1,
(ii) an alkylaluminum compound and,
(iii) optionally, an external electron donor compound.

13. The catalyst of claim 12, further comprising an external electron donor compound.

14. The catalyst of claim 13, wherein the external donor is selected from silicon compounds of the formula (R$_7$)$_a$(R$_8$)$_b$Si(OR$_9$)$_c$, where a and b are integers from 0 to 2, c is an integer from 1 to 4, the sum (a+b+c) is 4 and R$_7$, R$_8$, and R$_9$ are radicals with 1-18 carbon atoms optionally containing heteroatoms.

15. A process comprising the step of polymerizing one or more olefins of the formula CH$_2$=CHR, in which R is hydrogen or a hydrocarbyl radical with 1-12 carbon atoms, in the presence of a catalyst system comprising the product of the reaction between:
i. the solid catalyst component according to claim 1;
ii. an alkylaluminum compound and,
iii. optionally, an external donor compound.

* * * * *